(12) United States Patent
Cheon et al.

(10) Patent No.: US 8,288,586 B2
(45) Date of Patent: Oct. 16, 2012

(54) METHOD AND APPARATUS FOR SEPARATING AND REFINING HIGH PURITY 2,6-NAPHTHALENE DICARBOXYLIC ACID USING CRYSTALLIZATION

(75) Inventors: Yang-Ho Cheon, Gyeonggi-do (KR); Young-Gyo Choi, Gyeonggi-do (KR)

(73) Assignee: Hyosung Corporation, Seoul (KR)

( * ) Notice: Subject to any disclaimer, the term of this patent is extended or adjusted under 35 U.S.C. 154(b) by 301 days.

(21) Appl. No.: 12/675,403

(22) PCT Filed: Sep. 24, 2008

(86) PCT No.: PCT/KR2008/005661
§ 371 (c)(1),
(2), (4) Date: Feb. 26, 2010

(87) PCT Pub. No.: WO2009/045016
PCT Pub. Date: Apr. 9, 2009

(65) Prior Publication Data
US 2010/0256415 A1 Oct. 7, 2010

(30) Foreign Application Priority Data
Oct. 1, 2007 (KR) .................. 10-2007-0098917

(51) Int. Cl.
*C07C 63/36* (2006.01)

(52) U.S. Cl. ......................................... 562/490; 562/486
(58) Field of Classification Search ................ None
See application file for complete search history.

(56) References Cited

U.S. PATENT DOCUMENTS

| 5,449,820 A | 9/1995 | Fukui et al. |
| 6,194,609 B1 * | 2/2001 | Abrams et al. ............... 562/486 |
| 6,717,009 B2 * | 4/2004 | Motoyuki et al. ............ 562/486 |

FOREIGN PATENT DOCUMENTS

| JP | 9-71553 A | 3/1997 |
| WO | 01/16067 A2 | 3/2001 |
| WO | 2006/071025 A1 | 7/2006 |

* cited by examiner

*Primary Examiner* — Sudhakar Katakam
(74) *Attorney, Agent, or Firm* — Harness, Dickey & Pierce, PLC

(57) ABSTRACT

The present invention relates to a method for separating and refining high purity 2,6-naphthalene dicarboxylic acid having an excellent color and purity of 99.9% or more by using crude 2,6-naphthalene dicarboxylic acid. And more particularly, the present invention relates to a method for separating and refining 2,6-naphthalene dicarboxylic acid, in which adjustment of pressure and temperature during multiple-step crystallization process enables controlling nucleation and the crystal growth rate, thereby allowing a particle size distribution and form to be controlled.

11 Claims, 2 Drawing Sheets

METHOD AND APPARATUS FOR SEPARATING AND REFINING HIGH PURITY 2,6-NAPHTHALENE DICARBOXYLIC ACID USING CRYSTALLIZATION

TECHNICAL FIELD

The present invention relates to a method for refining of 2,6-naphthalene dicarboxylic acid (hereinafter referred to as "2,6-NDA") using crystallization. In accordance with the method, 2,6-naphthalene dicarboxylic acid having high yield as well as excellent purity and color can be obtained.

BACKGROUND ART

Polyethylene naphthalate (PEN) produced by the polymerization of 2,6-NDA and ethylene glycol are known to excel in several properties such as thermal stability, strength, measurement stability and gas permeability, etc. when compared with polyethylene terephthalate (PET). Based on these advantages, PEN is chosen as good materials for films, fibers and bottles, etc. In addition, PEN is highly resistant to diffusion of gases, it is useful for the manufacture of food containers and packaging materials. PEN can also be used as a material to replace high-priced tire cords. 2,6-naphthalene dicarboxylate (2,6-NDC) is a generally commercialized PEN monomer, as known in U.S. Pat. Nos. 5,254,719, 5,262,560, 6,211,398, and 6,013,831. At present, while 2,6-NDC is used as a major material of PEN, using 2,6-NDA is highly effective due to high yield and low production cost of polymers. Further, directly purifying crude-NDA prepared in the oxidation process, without converting it into 2,6-NDC, simplifies the process and lowers production costs. Moreover, in the polymerization process of 2,6-NDC, explosion-proof equipment is necessary because methanol is formed as a byproduct, whereas in the polymerization process of 2,6-NDA, water is formed, thus, such an additional equipment as above is unnecessary.

2,6-NDA is obtained by oxidizing 2,6-dimethyl naphthalene (hereinafter referred to as "2,6-DMN") in the presence of a heavy metal catalyst. However, the thus-obtained crude 2,6-NDA contains a large amount of numerous impurities as by-products such as 6-formyl-2-naphthoic acid(FNA), 6-methyl-2-naphthoic acid(MNA), trimellitic acid(TMLA), bromo naphthalene dicarboxylic acid(Br-NDA) and 2-naphthoic acid(NA) as well as catalytic metals such as cobalt and manganese.

PEN obtained by the polymerization of ethylene glycol and 2,6-NDA containing various impurities as mentioned above shows poor quality due to its low thermal resistance and softening point, and coloration. Accordingly, high purity 2,6-NDA having a purity of about 99.9 wt % is required to obtain high quality PEN.

Several methods for refining impurities of NDA to obtain high purity NDA have been known. U.S. Pat. Nos. 5,256,817 and 6,255,525 disclose a method for refining impurities by dissolving NDA in general solvents and hydrogenating it. Furthermore, U.S. Pat. No. 5,256,817 discloses a method for refining NDA using an acetic acid or an aqueous solution of acetic acid as a solvent, dissolving it at a high temperature, and then hydrogenating it. However, an excessive amount of naphthoic acid and tetralin dicarboxylic acid is easily produced due to decarbonation, a by-product of hydrogenation reaction. And it also requires expensive metal catalysts for hydrogenation, thereby it being economically disadvantageous.

U.S. Pat. No. 6,255,525 discloses a process of filtering insoluble substances by using water as a solvent, and impurities thereof are removed or converted into a removable form by hydrogenation. However, the process has disadvantages in that the NDA thus prepared has a high chromaticity and the catalyst has a short life time.

Japanese Patent Publication No. 62-2307 discloses a method of dissolving NDA in solvents such as dimethylsulfoxide, dimethylformamide, etc., removing insoluble substances and then recrystallizing it. However, such method requires a quantity of solvents and activated carbons, and 2,6-NDA is rarely soluble in the solvents thereof. Further, the solvents may be hydrogenated with impurities, making hydrogenation impossible, and the formyl naphthoic acid is not eliminated completely.

Japanese patent Publication No. 5-32586 A discloses a method for refining 2,6-NDA by dissolving it using pyridine or pyridine derivatives as a solvent and then crystallizing it, but this method is also problematic because the solubility of 2,6-NDA in the solvents is sensitive to temperature and its yield is thus low.

Korean Patent Publication 2006-009437 discloses a method of refining 2,6-NDA, comprising the steps of: mixing crude 2,6-NDA and amine compounds, and solvents and non-solvents; heating and dissolving the compounds thus prepared; cooling and filtering the mixture to obtain an amine salt crystal of 2,6-NDA; and heating the amine salt crystal of 2,6-NDA to deaminate the salt. However, this method is too complicated and has a low yield per unit in each process. Moreover, the method is not economically advantageous as expensive amine compounds are used.

U.S. Pat. No. 5,563,294 discloses a method for producing 2,6-NDA by esterifying NDC, followed by removal of methanol and crystallization. But the method comprises multiple complicated processes, and as such is not economically efficient.

As another method for refining 2,6-NDA, there is a method of converting NDA into its metal salt and then dissolving and recrystallizing it. Japanese Patent Publication No. 52-20993 A discloses a method for refining 2,6-NDA by dissolving it in alkali aqueous solutions such as KOH or NaOH with pH adjusted to thereby prepare its alkali metal salt, then absorbing it with a solid absorbent and crystallizing it. Disproportionation of the thus-produced mono alkali salt with water generates a refined 2,6-NDA. However, this method requires a quantity of solid absorbents and solvents, and as all mono alkali salts are crystallized, salts generated by impurities such as NA or FNA, etc. are also crystallized, thus making it difficult to separate them. Further, alkali metal remains in the crystal of NDA, thereby deteriorating chromaticity when polymerizing, and causing disadvantages in terms of a crystal size and yield.

Therefore, a simple and easy process to obtain high purity 2,6-NDA having excellent color and purity as well as high yield in an economical manner is required.

The above-said refining methods use relatively complicated processes and expensive solvents, or additional reaction processes are necessary. Such methods produce impurities in the process due to by-products and additives, thereby leading to an additional process for treating such impurities, and making the methods economically disadvantageous.

DISCLOSURE OF INVENTION

[Technical Problem]

Thus, in order to solve the problems in prior arts as described above, the present invention provides a method and apparatus for producing 2,6-NDA by refining crude 2,6-NDA. The method thereof includes simply controlling crystallizing process without any additional procedures, thereby obtaining high purity 2,6-NDA having a purity of 99.9% with a particle size distribution suitable for polymerization.

[Technical Solution]

In order to achieve the above object, the present invention relates to a process for separating and refining 2,6-NDA by using crude NDA having a relatively high purity to thereby obtain high purity 2,6-NDA. The separation and refinement process of crude NDA having a purity of 98.0% to 99.5 wt % based on the weight of NDA comprises the steps of:
1) mixing crude 2,6-NDA and water in a certain ratio to make a slurry;
2) dissolving the mixed slurry;
3) performing crystallization to grow the dissolved mixture into crystals;
4) washing the crystals thus obtained;
5) performing a solid-liquid separation to separate 2,6-NDA and water after washing; and
6) drying 2,6-NDA.

[Advantageous Effects]

The refining methods in prior arts use relatively complicated processes and expensive solvents, or additional reaction processes are necessary. Such methods produce impurities due to by-products and additives in the process, thereby leading to an additional process for treating such impurities, and making it economically disadvantageous with relatively low yield. However, the present invention simply controls a crystallizing process without an additional reaction process, thereby obtaining high purity 2,6-NDA having a purity of more than 99.9% and a yield of more than 92%, with a particle size distribution suitable for polymerization. Moreover, the heat generated in each multiple-step crystallization is collected to be used as an energy source for dissolving early 2,6-NDA, enabling high purity 2,6-NDA to be produced in a more economical and energy-saving.

MODE FOR THE INVENTION

Figure 1:
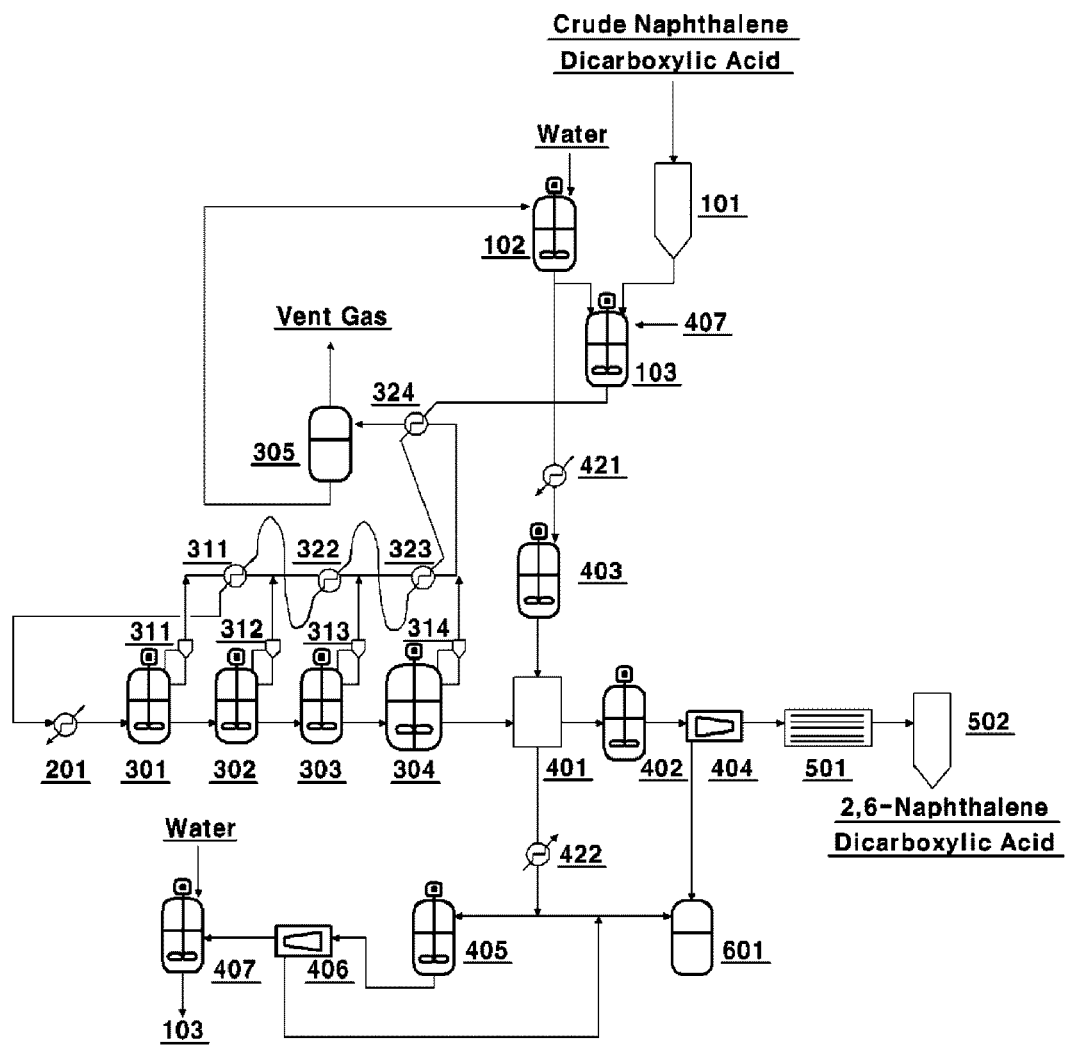
FIG. 1 is a schematic illustration showing an entire process for separation and refinement of 2,6-NDA according to the present invention.

The present invention provides a method for separating and refining 2,6-NDA from crude 2,6-NDA having a purity of 98.0~99.5%, comprising the steps of:
1) mixing crude 2,6-NDA and water in a certain ratio to make a slurry;
2) dissolving the mixed slurry;
3) performing crystallization to grow the dissolved mixture into crystals
4) washing the crystals obtained;
5) performing solid-liquid separation to separate 2,6-NDA and water after washing; and
6) drying 2,6-NDA.

In the present invention, 2,6-NDA is refined in the presence of a bromine/manganese/cobalt catalyst. And 2,6-DMN is reacted with air and diluted gas in the presence of acetic acid to produce high purity 2,6-NDA having a purity of 98.0% to 99.5%. The composition of 2,6-NDA is shown in table 1.

TABLE 1

| Purity (%) | Impurities (%) | | | |
|---|---|---|---|---|
| 2,6-NDA | NA | MNA | TMLA | FNA |
| 98.0000%~99.50000% | 0.3000%~0.0500% | 0.1000%~0.0500% | 0.5000%~0.1500% | 0.2000%~0.0500% |

| Purity (%) | Impurities (%) | | | Inorganic metal impurities (ppm) | |
|---|---|---|---|---|---|
| 2,6-NDA | Br-NDA | Heavy | unknown | Co | Mn |
| 98.0000%~99.50000% | 0.1000%~0.0500% | 0.3000% 0.0500% | 0.5000%~0.1000% | 15~50 ppm | 10~15 ppm |

| | Purity (%) | Inorganic metal impurities (ppm) | | | chromaticity | | Average crystal |
|---|---|---|---|---|---|---|---|
| | 2,6-NDA | Br | Fe | Na | L* | b* | size (μm) |
| | 98.0000%~99.50000% | 50~70 ppm | 2~15 ppm | 3~19 ppm | 65~80 | 12~20 | 5~15 μm |

*L: Lightness, b: Yellow chromaticity

The separation and refinement process including the crystallization process of 2,6-NDA containing the above composites in table 1 will be described in detail with reference to FIG. 1.

Crude 2,6-NDA is moved to a material storage tank 101 and water to be used as a refining solvent is fed into a water storage tank 102 at a certain feed rate. Crude 2,6-NDA and water is fed into a slurry mixing tank 103, and well dispersed. The mixing process is carried out in consideration of solubility of crude 2,6-NDA and water. The concentration is preferably in the range of 5 to 10%. Specifically, the dissolving ratio of 2,6-NDA in water is 3% at the temperature of 270° C., 5% at 283° C., 7% at 291° C. and 10% at 300° C. Further, part of 2,6-NDA slurry is separated from the mother liquid in a storage tank of reflux mother liquid powder 407, and it is fed into the slurry mixing tank 103 with its concentration adjusted to the above level. 2,6-NDA slurry, well mixed in the slurry mixing tank 103, is primarily preheated using heat generated at the top during a first to fourth crystallization processes to be partly dissolved, and using dissolving preheater 201, it is entirely dissolved to be fed into a first crystallization unit 301 at a certain feed rate.

The temperature at the rear end after the process in the preheater is set at 310° C., and the resultant slurry is transferred into the first crystallization unit 301 at a certain influx rate. Nucleation occurs in the crystallization unit 301, thereby crystallizing 2,6-NDA. The process in the first crystallization unit 301 is carried out for 30 to 90 minutes with a pressure of 85 kg/cm$^2$ at a temperature of 280° C. A pressure control device is installed at the upper part of the first crystallization unit 301 in order to adjust pressure and temperature thereof. Gas moving upward is condensed into water and transferred into a circular flash drum 305. Water condensed at the bottom of the circular flash drum 305 is transferred into water storage tank 102, and 2,6-NDA powder, part of which moves to the upper part with water, is filtered through a first powder-separation unit 311, returning to the first crystallization unit 301. 2,6-NDA nuclide and crystal formed in the crystallization unit 301 is transferred into a second crystallization unit 302 at a certain influx rate. A second 302, a third 303 and a fourth 304 crystallization units have the same principle and structure as the first crystallization unit 301.

A process in each crystallization unit is carried out preferably for 30 to 90 minutes. The time set is for separation and refinement with aimed purity and yield in consideration of the growing progress of the 2,6-NDA crystal. Two to four crystallization units may be linked to each other. In consideration of the growth of crystal and supersaturation, etc., temperature and pressure conditions should be adjusted depending on the number of crystallization units linked in order to achieve desired purity, yield and a particle size. The reason to link two to four crystallization units is to adjust a required temperature in accordance with a drop in pressure, thereby controlling supersaturation degree and the crystal growth rate at $1 \times 10^{-6} \sim 1 \times 10^{-9}$ m/s. By that process, impurities are kept from being contained in the crystal, enabling the crystal to have a certain size to grow and thereby producing high purity 2,6-NDA.

According to the present invention, series-linked four crystallization units are the most preferable form in terms of particle size and distribution, purity and yield of the crystallization. In the case that the four crystallization units are linked in series, the temperature and pressure of the four crystallization units are set at 260~280° C. and 60~85 kg/cm$^2$, respectively, in the first crystallization unit, at 240~260° C. and 40~65 kg/cm$^2$ in the second, at 220~240° C. and 30~45 kg/cm$^2$ in the third, and at 200~220° C. and 20~35 kg/cm$^2$ in the fourth crystallization unit. By that process, supersaturation is formed with a preferable range of crystal growing speed, thereby enabling separation and refinement of 2,6-NDA with high purity and high yield, and having a desired particle size of 35 to 75 μm.

In the case of linking two crystallization units, it is preferable that the temperature and pressure of the two crystallization units are set at 250 to 260° C. and 60 to 75 kg/cm$^2$, respectively, in a first crystallization unit, and at 200 to 240° C. and 25 to 45 kg/cm$^2$ in a second crystallization unit. In the case of linking three crystallization devices, the temperature and pressure of the three crystallization units are each set at 260 to 280° C. and 60 to 85 kg/cm$^2$ in a first crystallization unit, at 240 to 260° C. and 40 to 65 kg/cm$^2$ in a second crystallization unit, and at 200 to 220° C. and 20 to 35 kg/cm$^2$ in a third crystallization unit. By that process, 2,6-NDA having a desired purity, yield and particle size can be obtained.

After the process in the crystallization unit, the crystal is transferred to a washing unit 401 to be primarily filtered.

Water, becoming hot after passing through solvent preheater 421 from a water storage tank 102, is fed and stored in a hot solvent storage tank 403. The water stored is then transferred to the washing unit 401 where the primarily filtered crystal powder stores. After the water is washed therein, it is transferred to reslurry drum 402, and then to a high-speed centrifugal solid-liquid separation unit 404 at a certain influx rate. 2,6-NDA crystal is separated therein and dried in a drying unit 501 to be stored in a 2,6-NDA tank 502.

Mother liquid additionally washed in a washing unit passes through a cooling condenser 422 to thereby be crystallized, which is then fed into a mother liquid storage tank 405. The fed slurry is separated with a mother liquid separation unit 406. And the powder separated is stored in a reflux mother liquid powder storing unit 407 and then fed at a certain feed rate into a material slurry mixing tank 103 to be circulated. The circulation can increase production yield. The circulation amount is determined depending on a material composition. A secondary mother liquid separated in the mother liquid separation unit 406 is sent to a waste storage tank 601. Some of the liquid in the washing unit 401 as well as some separated waste liquid in the high-speed centrifugal solid-liquid separation unit 404 is sent to the waste storage tank 601.

With the above units and methods of the present invention, 2,6-NDA having high purity is obtained with high yield by controlling the crystal growing speed, form and particle size.

Hereinafter, the present invention will be described in detail with reference to Examples. However it should not be construed that the scope of the invention is limited thereto.

EXAMPLE 1

Crude 2,6-NDA having a purity of 98.0~99.5% is mixed with water to prepare a slurry having a concentration of 7%. The slurry thus prepared passes through a heat exchanger at the top of the crystallization unit at a rate of 80 L/hr, primarily preheated with some melted. And through the preheater, its temperature of 310° C. is maintained. The first crystallization unit has a temperature of 260° C. with a pressure of 65 kg/cm$^2$, and the second has a temperature of 215° C. with a pressure of 25 kg/cm$^2$ to grow 2,6-NDA crystal. Condensed water is discharged to the upper part of the crystallization unit due to a drop in pressure, which is about 10% of the slurry mass. The remaining crystal slurry is transferred to the washing unit to be filtered primarily.

After the filtration, hot water at 215° C. is fed to the inside of the washing unit for washing twice. After the washing, filtered crystal powder and water having ten times more weight of that crystal powder is sent to the reslurry storage tank, from which reslurry is then sent to the solid-liquid separation unit at a rate of 62 L/hr in order to separate solid and liquid. A certain amount of separated crystal powder is continuously sent to a drying unit to be dried at 130° C., thereby obtaining 2,6-NDA. The analysis result of 2,6-NDA thus produced is shown in table 2.

TABLE 2

| Purity (%) 2,6-NDA | Impurities (%) | | | | | | | | Yield (%) |
|---|---|---|---|---|---|---|---|---|---|
| | NA | MNA | TMLA | FNA | DCT | Br-NDA | Heavy | Unknown | |
| 99.9014 | 0.0840 | N/A | NA/ | N/A | N/A | 0.0250 | 0.0158 | 0.0158 | 94.5 |

| Purity (%) 2,6-NDA | Inorganic metal impurities (ppm) | | | | | Chromaticity | | Average crystal size (μm) |
|---|---|---|---|---|---|---|---|---|
| | Co | Mn | Br | Fe | Na | L* | b* | |
| 99.9014 | N/A | N/A | N/A | 2-3 | 2 | 95.3 | 4.76 | 35-45 |

*Detection limit = less than 1 ppm, N/A = no detection
*L: Lightness, b: Yellow chromaticity

COMPARATIVE EXAMPLE 1

The process was carried out in the same manner as Example 1, except that the temperature and pressure of the first crystallization unit is set at 240° C. and 45 kg/cm², respectively, and at 180° C. and 15 kg/cm² in the second crystallization unit. The result is shown in table 3.

TABLE 3

| Purity (%) 2,6-NDA | Impurities(%) | | | | | | | | Yield (%) |
|---|---|---|---|---|---|---|---|---|---|
| | NA | MNA | TMLA | FNA | DCT | Br-NDA | Heavy | Unknown | |
| 99.8752% | 0.0840% | N/A | NA/ | N/A | N/A | 0.0250 | 0.0250% | 0.0158% | 89.5 |

| Purity (%) 2,6-NDA | Inorganic metal impurities (ppm) | | | | | Chromaticity | | Average crystal size (μm) |
|---|---|---|---|---|---|---|---|---|
| | Co | Mn | Br | Fe | Na | L* | b* | |
| 99.8752% | N/A | N/A | 5~15 | 2-3 | 2 | 92.3 | 6.32 | 15~20 |

*L: Lightness, b: Yellow chromaticity

EXAMPLE 2

The process is carried out in the same manner as Example 1, except that three crystallization units are linked, wherein the temperature and pressure of the three crystallization units are each set at 260 to 280° C. and 60 to 85 kg/cm² in the first crystallization unit, 240 to 260° C. and 40 to 65 kg/cm² in the second, and 200 to 220° C. and 20 to 35 kg/cm² in the third. The result is shown in table 4.

TABLE 4

| Purity (%) 2,6-NDA | Impurities (%) | | | | | | | | Yield (%) |
|---|---|---|---|---|---|---|---|---|---|
| | NA | MNA | TMLA | FNA | DCT | Br-NDA | Heavy | Unknown | |
| 99.9265% | 0.0557 | N/A | NA/ | N/A | N/A | N/A | 0.0122 | 0.0056 | 93.9 |

| Purity (%) 2,6-NDA | Inorganic metal impurities (ppm) | | | | | Chromaticity | | Average crystal size (μm) |
|---|---|---|---|---|---|---|---|---|
| | Co | Mn | Br | Fe | Na | L* | b* | |
| 99.9265% | N/A | N/A | 5~15 | Less than 2 | Less than 2 | 95.8 | 3.38 | 35~55 |

*L: Lightness, b: Yellow chromaticity

EXAMPLE 3

Figure 2:
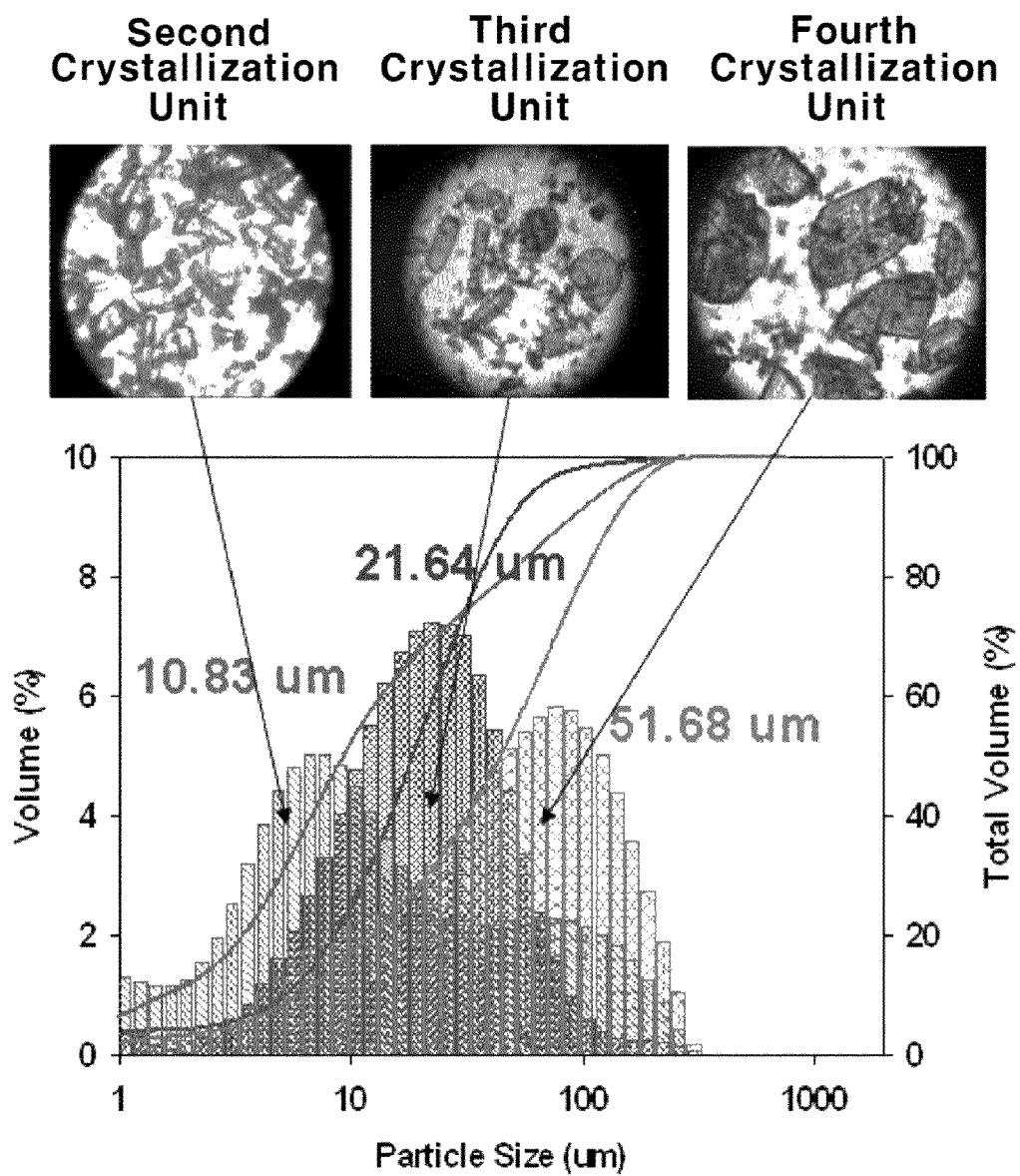
FIG. 2 is a photograph and a graph each showing a particle size and distribution of 2,6-NDA after a second, third and fourth crystallization processes.

The process is carried out in the same manner as Example 1, except that four crystallization units are linked, wherein the temperature and pressure of the four crystallization units are each set at 260 to 280° C. and 60 to 85 kg/cm², in the first crystallization unit, at 240 to 260° C. and 40 to 65 kg/cm² in the second, and at 220 to 240° C. and 30 to 45 kg/cm² in the third, and in the fourth at 200 to 220° C. and 20 to 35 kg/cm². The analysis result on the crystals obtained is shown in table 5. FIG. 2 is a photograph showing the particle size and distribution of the crystals obtained in the second, third and fourth crystallization processes.

TABLE 5

| Purity (%) | Impurities (%) | | | | | | | | |
|---|---|---|---|---|---|---|---|---|---|
| 2,6-NDA | NA | MNA | TMLA | FNA | DCT | Br-NDA | Heavy | Unknown | Yield (%) |
| 99.9519% | 0.0327 | N/A | N/A | N/A | N/A | N/A | 0.0117 | 0.0037 | 94.1 |

| Purity (%) | Inorganic metal impurities (ppm) | | | | | Chromaticity | | Average crystal |
|---|---|---|---|---|---|---|---|---|
| 2,6-NDA | Co | Mn | Br | Fe | Na | L* | b* | size (μm) |
| 99.9519% | N/A | N/A | N/A | Less than 2 | Less than 2 | 96.7 | 3.31 | 40~75 |

*L: Lightness, b: Yellow chromaticity

COMPARATIVE EXAMPLE 2

The process was carried out in the same manner as Example 1, except that four crystallization units were linked, wherein the temperature and pressure of the four crystallization units are each set at 250° C. and 55 kg/cm² respectively in the first crystallization unit, in the second, at 230° C. and 45 kg/cm², in the third at 210° C. and 25 kg/cm² and in the fourth at 180° C. and 15 kg/cm². The result obtained is shown in table 6.

TABLE 6

| Purity (%) | Impurities (%) | | | | | | | | |
|---|---|---|---|---|---|---|---|---|---|
| 2,6-NDA | NA | MNA | TMLA | FNA | DCT | Br-NDA | Heavy | Unknown | Yield (%) |
| 99.8984% | 0.0757 | N/A | N/A | N/A | N/A | N/A | 0.0153 | 0.0106 | 90.8 |

| Purity (%) | Inorganic metal impurities (ppm) | | | | | Chromaticity | | Average crystal |
|---|---|---|---|---|---|---|---|---|
| 2,6-NDA | Co | Mn | Br | Fe | Na | L* | b* | size (μm) |
| 99.8984% | N/A | N/A | 2~5 | Less than 2 | Less than 2 | 95.5 | 3.78 | 18~30 |

*L: Lightness, b: Yellow chromaticity

COMPARATIVE EXAMPLE 3

The refinement of 2,6-NDA is carried out in the same manner as in Example 2 of Korean Patent Publication No. 2006-0079437 and the result is shown in table 7. 50.0 g of crude 2,6-NDA and 60.0 g of triethyl amine were added to a 1-neck Erlenmeyer flask having a Pyrex-type lid at room temperature and room pressure. And 400 g of a mixed solution containing methanol:water:methyl acetate in a ratio of 17.5:2.5:80.0 by weight were added thereto and the mixture was then stirred for 30 minutes at a temperature of 60° C. to obtain a solution of amine salt of 2,6-NDA. The amine salt solution was filtrated using a filter with a 7 μm pore size at 60° C. The thus-obtained filtrate was heated to remove part of solvent therein. The concentrate prepared was cooled to a room temperature and stirred slowly for one hour to obtain amine salt crystal of 2,6-NDA. The crystal was collected and dissolved into 400 g of a mixed solution containing methanol:water:methyl acetate in a volume ratio of 17.5:2.5:80.0 to be recrystallized in the same manner as above, thereby obtaining amine salt crystal of 2,6-NDA. A mixed solution containing the crystal was filtered to separate the crystal, and then it was placed for 1 hour at 90° C. to remove a solvent, thereby obtaining purified 2,6-NDA.

TABLE 7

| Purity (%) | Impurities (%) | | | | | | | | |
|---|---|---|---|---|---|---|---|---|---|
| 2,6-NDA | NA | MNA | TMLA | FNA | DCT | Br-NDA | Heavy | Unknown | Yield (%) |
| 99.6391% | 0.0081 | 0.026 | 0.0200 | 0.0022 | N/A | 0.0039 | 0.1692 | 0.0638 | 82.24 |

| Purity (%) | Inorganic metal impurities (ppm) | | | | | Chromaticity | | crystal |
|---|---|---|---|---|---|---|---|---|
| 2,6-NDA | Co | Mn | Br | Fe | Na | L* | b* | size (mm) |
| 99.6391% | N/A | N/A | 10~15 | 2~5 | 2~7 | 95.7 | 3.31 | 1~20 mm |

*L: Lightness, b: Yellow chromaticity

COMPARATIVE EXAMPLE 4

The process was carried out in the same manner as Example 4, except that a hydrogenation reaction was added thereto. 0.5 wt % of palladium-carbon(Pd/C) obtained from Engelhard Corporation was used as a catalyst in the hydrogenation reaction. Hydrogen was inserted into the upper part of a reactor, and the preheater after a hydrogen reactor was installed. The refinement result is shown in table 8.

TABLE 8

| Purity (%) | Impurities (%) | | | | | | | | Yield (%) |
|---|---|---|---|---|---|---|---|---|---|
| 2,6-NDA | NA | MNA | TMLA | FNA | DCT | Br-NDA | Heavy | Unknown | |
| 99.5769% | 0.1327 | N/A | N/A | N/A | 0.1350 | N/A | 0.0517 | 0.1037 | 87.1 |

| Purity (%) | Inorganic metal impurities (ppm) | | | | | Chromaticity | | Average crystal size (mm) |
|---|---|---|---|---|---|---|---|---|
| 2,6-NDA | Co | Mn | Br | Fe | Na | L* | b* | |
| 99.5769% | N/A | N/A | N/A | 2~7 | 3~10 | 94.1 | 5.35 | 35~50 mm |

*L: Lightness, b: Yellow chromaticity

The invention claimed is:

1. A method for separating and refining 2,6-naphthalene dicarboxylic acid from crude 2,6-naphthalene dicarboxylic acid having a purity of 98.0~99.5%, comprising the steps of:

(a) mixing crude 2,6-naphthalene dicarboxylic acid and water to prepare slurry;

(b) dissolving the mixed slurry;

(c) performing crystallization to grow the dissolved mixture into crystals through multiple-step crystallization using a plurality of crystallization units;

(d) washing the crystals obtained;

(e) performing solid-liquid separation to separate 2,6-naphthalene dicarboxylic acid and water after washing; and (f) drying 2,6-naphthalene dicarboxylic acid;

wherein:

the plurality of crystallization units linked in series is four crystallization units, and the temperature and pressure thereof are set at 260-280° C. and 60-85 kg/cm$^2$, respectively, in a first crystallization unit, at 240-260° C. and 40-65 kg/cm$^2$ in a second, 220-240° C. and 30-45 kg/cm$^2$ in a third and 200-220° C. and 20-35 kg/cm$^2$ in a fourth;

the plurality of crystallization units linked in series is two crystallization units, and the temperature and pressure thereof are set at 250-260° C. and 60-75 kg/cm$^2$, respectively, in a first crystallization unit and at 200-240° C. and 25-45 kg/cm$^2$, respectively, in a second; or the plurality of crystallization units linked in series is three crystallization units, and the temperature and pressure thereof are set at 260-280° C. and 60-85 kg/cm$^2$, respectively, in a first crystallization unit, at 240-260° C. and 40-65 kg/cm$^2$ in a second and at 200-220° C. and 20-35 kg/cm$^2$ in a third.

2. The method for separating and refining 2,6-naphthalene dicarboxylic acid according to claim 1, wherein the slurry mixed in the dissolving step is primarily preheated using heat generated at the upper part of a crystallization unit, and then the slurry is entirely dissolved after passing through the preheater to thereby have a constant temperature of 290~310° C.

3. The method for separating and refining 2,6-naphthalene dicarboxylic acid according to claim 1, wherein the concentration of the slurry produced in the mixing step is in the range of 5 to 10%.

4. The method for separating and refining 2,6-naphthalene dicarboxylic acid according to claim 1, wherein the crystallization process lasts 30 to 90 minutes.

5. The method for separating and refining 2,6-naphthalene dicarboxylic acid according to claim 1, wherein the crystal growth rate is at $1\times10^{-6} \sim 1\times10^{-9}$ m/s.

6. The method for separating and refining 2,6-naphthalene dicarboxylic acid according to claim 1, wherein the size of the separated and refined crystal is 35~75 μm.

7. The method for separating and refining 2,6-naphthalene dicarboxylic acid according to claim 1, wherein the value of chromaticity b of the crystals is 5 or below, and the value of chromaticity L of the crystals is 95 or above.

8. The method of claim 1, wherein the product of step b) is fed into a first crystallization unit.

9. The method of claim 8, wherein the product fed into the first crystallization unit is at a temperature of 290-310° C.

10. The method of claim 1, wherein the crude naphthalene dicarboxylic acid has an average crystal size of 5-15 μm and the average crystal size of the product of step f) is 35-75 μm.

11. The method of claim 1, wherein the crude 2,6-naphthalene dicarboxylic acid of step a) comprises:

0.05-0.30 weight % 2-naphthoic acid;

0.05-0.10 weight % 6-methyl-2-naphthoic acid;

0.15-0.50 weight % trimellitic acid;

0.05-0.20 weight % 6-formyl-2-naphthoic acid; and 98.00-99.50 weight % 2,6-naphthalene dicarboxylic acid.

* * * * *